(12) United States Patent
Hacker

(10) Patent No.: US 12,290,417 B1
(45) Date of Patent: May 6, 2025

(54) MULTI-AXIS TUMOR MARGIN MARKER SYSTEM

(71) Applicant: Robert I. Hacker, Frontenac, MO (US)

(72) Inventor: Robert I. Hacker, Frontenac, MO (US)

(*) Notice: Subject to any disclaimer, the term of this patent is extended or adjusted under 35 U.S.C. 154(b) by 0 days.

(21) Appl. No.: 19/000,663

(22) Filed: Dec. 23, 2024

Related U.S. Application Data

(63) Continuation of application No. PCT/US2024/016778, filed on Feb. 21, 2024.

(60) Provisional application No. 63/447,334, filed on Feb. 21, 2023.

(51) Int. Cl.
*A61B 90/00* (2016.01)

(52) U.S. Cl.
CPC ...... *A61B 90/39* (2016.02); *A61B 2090/3908* (2016.02); *A61B 2090/3966* (2016.02); *A61B 2090/3987* (2016.02); *A61B 2090/3991* (2016.02)

(58) Field of Classification Search
CPC .............. A61B 90/34; A61B 2090/3904–3995
See application file for complete search history.

(56) References Cited

U.S. PATENT DOCUMENTS

| | | | |
|---|---|---|---|
| 6,146,373 A * | 11/2000 | Cragg | A61B 17/12186 604/48 |
| 6,161,034 A | 12/2000 | Burbank et al. | |
| 7,524,374 B2 | 4/2009 | Patrick et al. | |
| 8,114,006 B2 | 2/2012 | Fox et al. | |
| 8,600,481 B2 | 12/2013 | Sirimanne et al. | |
| 10,286,114 B2 | 5/2019 | Hermann et al. | |
| 11,219,502 B2 | 1/2022 | Liu | |
| 11,324,567 B2 | 5/2022 | Liu | |
| 2002/0193677 A1 | 12/2002 | Thornton | |
| 2006/0235365 A1 | 10/2006 | Terwilliger et al. | |
| 2010/0204570 A1 * | 8/2010 | Lubock | A61B 90/39 600/426 |
| 2011/0004094 A1 * | 1/2011 | Stubbs | A61B 90/94 250/492.1 |
| 2015/0148837 A1 * | 5/2015 | Shinar | A61B 17/12036 606/200 |
| 2019/0076212 A1 * | 3/2019 | Liu | A61B 90/39 |
| 2019/0231473 A1 * | 8/2019 | Liu | A61B 90/39 |
| 2020/0085497 A1 | 3/2020 | Zhang et al. | |
| 2021/0114088 A1 | 4/2021 | Hennessy et al. | |

(Continued)

*Primary Examiner* — Serkan Akar
*Assistant Examiner* — Younhee Choi
(74) *Attorney, Agent, or Firm* — Invention To Patent Services; Alex Hobson

(57) ABSTRACT

A multi-axis tumor excision marker system is configured to deposit markers along multiple axes radially about a tumor to define a boundary of margin tissue for excision. A catheter may deploy a marker extension that extends to a margin tissue boundary for depositing the marker. The marker extension may be a shape memory material that extends radially outward from catheter opening or may be directed radially outward by a guide head. The radiopaque marker may be a phase change marker, such as an adhesive that changes from a liquid to a solid. A marker may be a discrete marker and may have an extension portion that extends from an anchor portion. An envelopment marker has a plurality of marker extensions that each extend along an offset axis from each other. A spiral maker includes a maker extension that spirals around the margin boundary tissue.

9 Claims, 12 Drawing Sheets

(56) References Cited

U.S. PATENT DOCUMENTS

2021/0275276 A1\* 9/2021 Habibi .................... A61B 6/02
2022/0218392 A1 7/2022 Gross et al.

\* cited by examiner

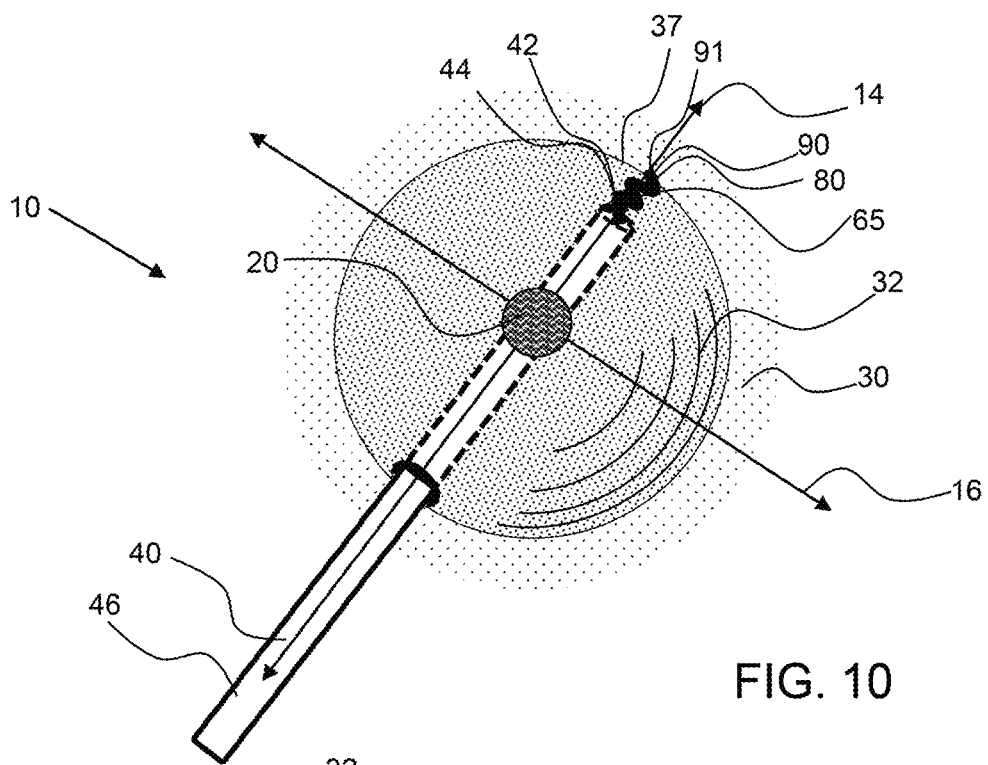
FIG. 10
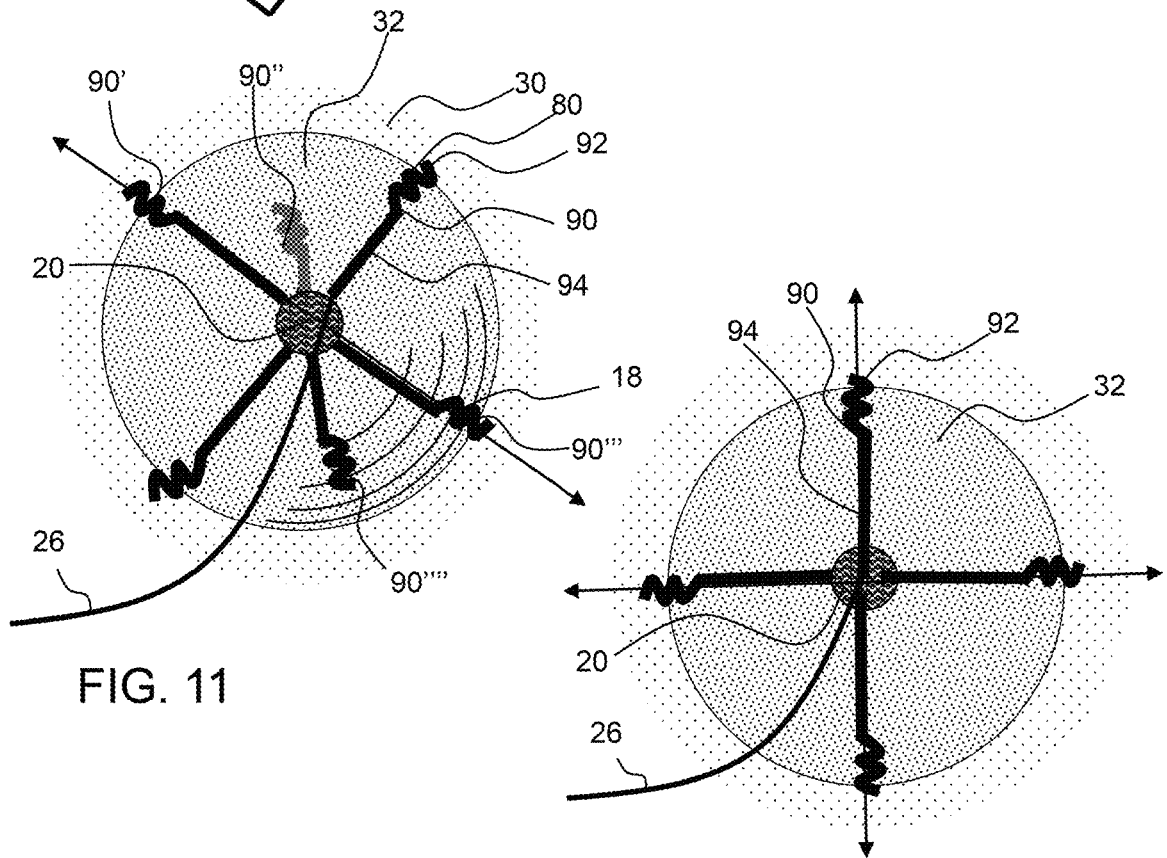
FIG. 11
FIG. 12

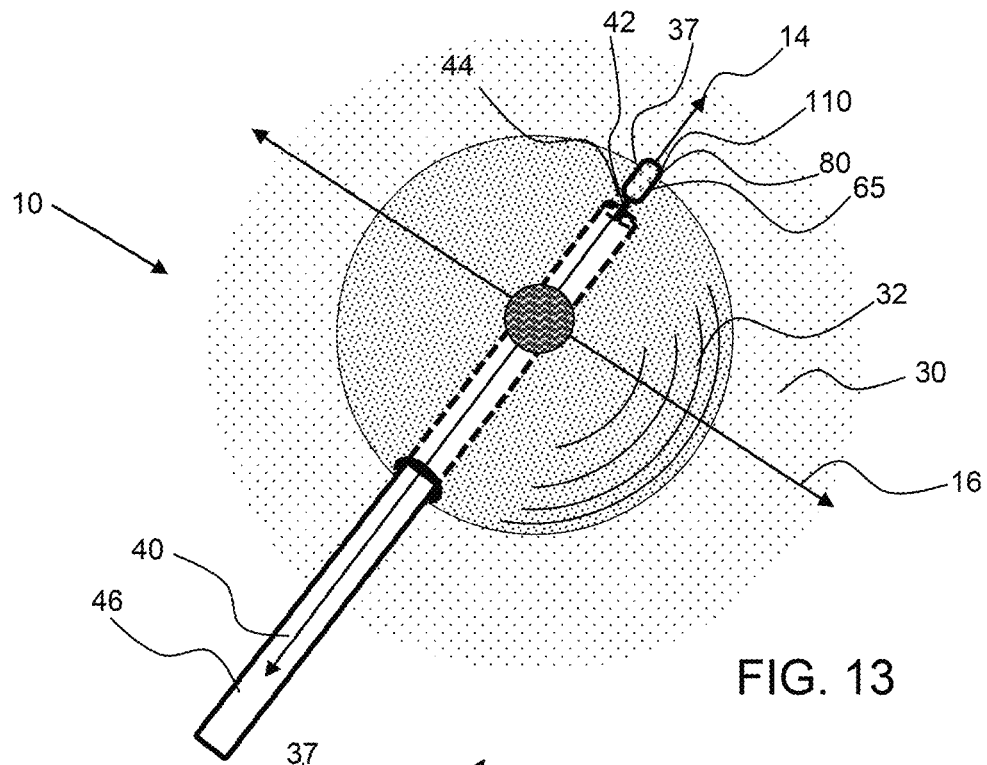
FIG. 13
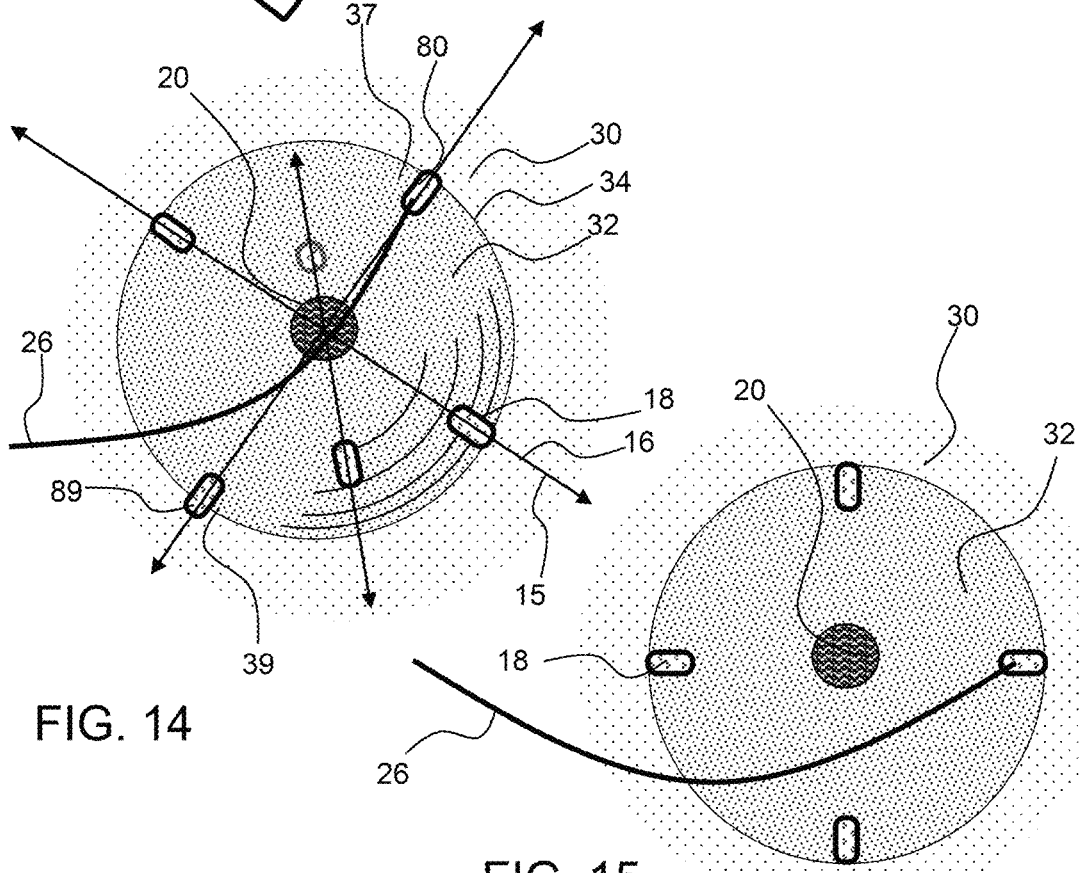
FIG. 14
FIG. 15

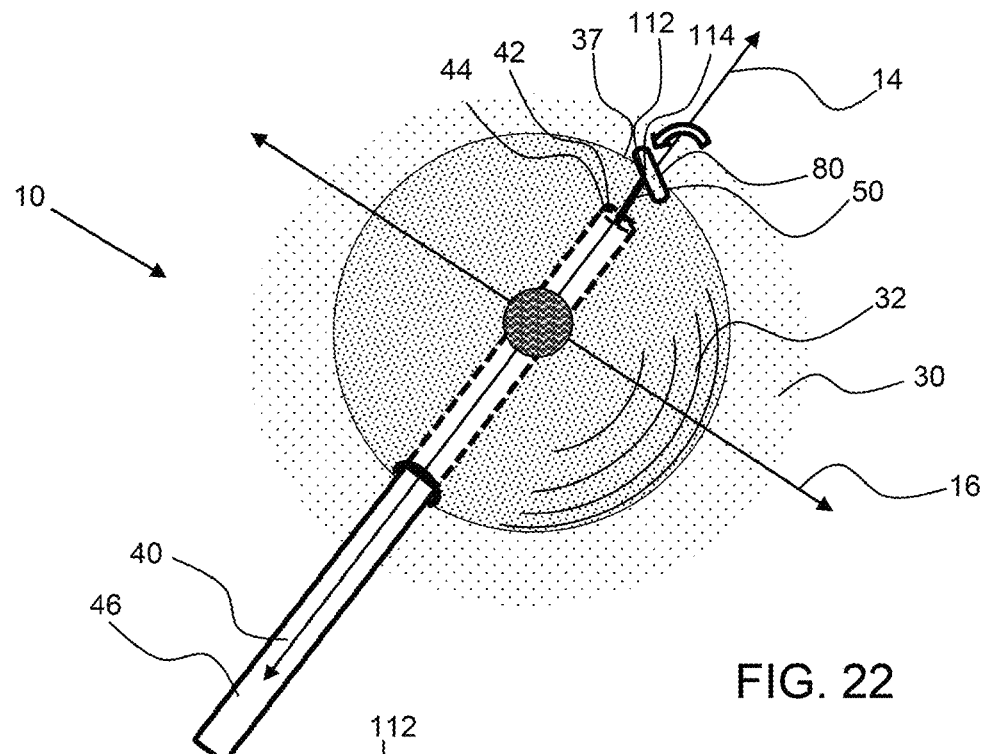
FIG. 22
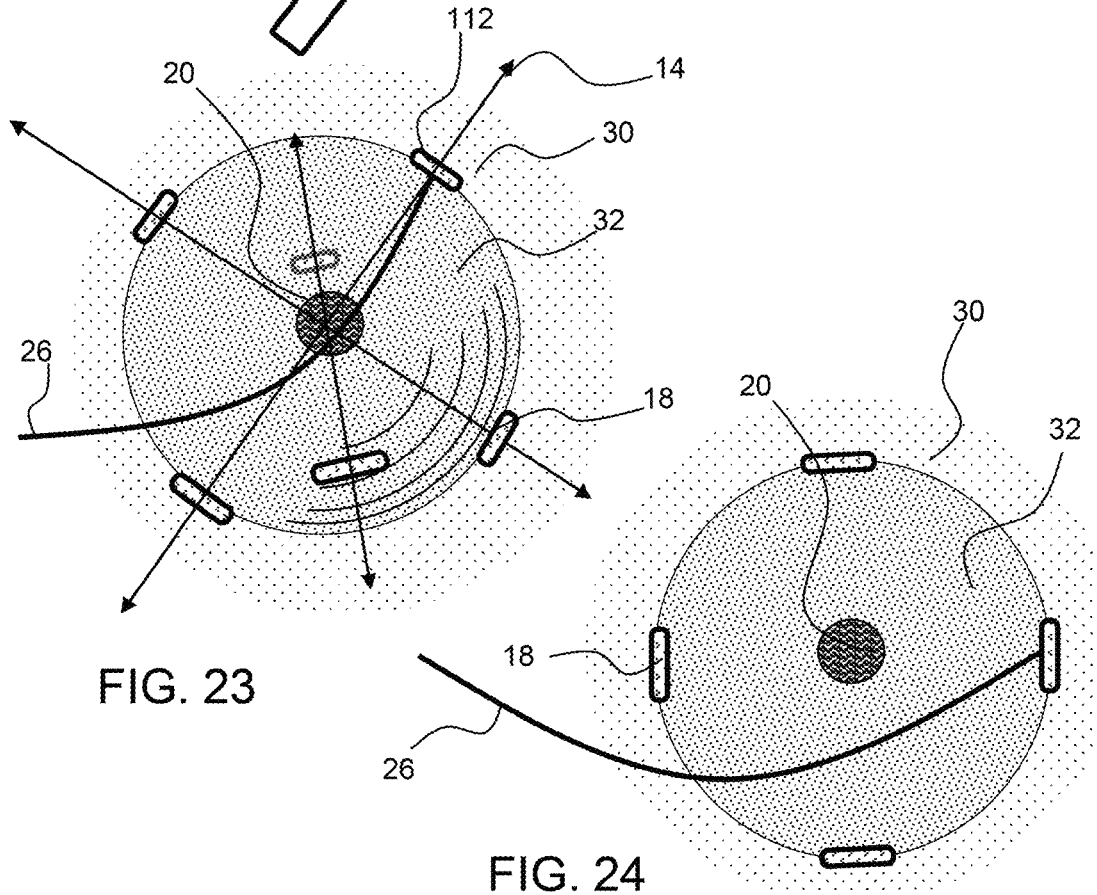
FIG. 23
FIG. 24

MULTI-AXIS TUMOR MARGIN MARKER SYSTEM

Cross Reference To Related Applications

This application is a continuation of International application No. PCT/US2024/016778, filed on Feb. 21, 2024, which claims the benefit of priority to U.S. provisional patent application No. 63/447,334, filed on Feb. 21, 2023; the entirety of all prior applications are hereby incorporated by reference.

BACKGROUND OF THE INVENTION

Field of the Invention

The invention relates to a multi-axis tumor marker system that is configured deposit one or more markers along multiple axes radially about a tumor to define a boundary of margin tissue for excision to aid in the identification and resection of an identified tumor.

Background

Excision of tumors requires removing margin tissue around the tumor to ensure that the entirety of the tumor is removed. These margins are defined by tumor type, location and scientific research. Having an appropriate "tumor free margin" is critical to patient long and short-term morbidity and survival. Trace lines or often a marking wire are deposited by a needle to assist a surgeon with the identification and resection of a tumor. Markers are often placed to indicate a margin around the tumor but current techniques typically only place a few markers in a region of interest leaving a large majority of the margin resection to be defined by the surgeon. This allows for a significant error rate in the field of tumor resection as the determination of the extent of margin tissue is largely subjective. Techniques for placing markers around a tumor can require advancing a needle or catheter past the tumor or legion, which poses a risk of disrupting the tumor. Additionally, markers are typically small radiopaque metal clips or beads with little gross visibility in-situ, making real time intraoperative identification difficult or impossible without adjunct imaging devices.

SUMMARY OF THE INVENTION

The invention is directed to a multi-axis tumor marker system that is configured to deposit one or more markers along multiple axes radially about a tumor to define a boundary of margin tissue for excision. The system may utilize a catheter to deploy a marker in the margin tissue about a tumor. A marker may be positioned by a marker extension that extends from the catheter to a boundary of the margin tissue to deposit the marker before being retracted back into the catheter. The marker extension may be a shape memory material that extends radially outward from catheter opening or may be directed radially outward by a guide head coupled to the catheter. The marker may be radiopaque, such as a metal or may be a phase change marker, such as an adhesive that changes from a liquid to a solid. A marker may be a discrete marker, or seed type marker, or may have an extension portion that extends from an anchor portion that is configured at the boundary of the margin tissue. A marker may have a plurality of extension portions that extend along the boundary of the margin tissue. The plurality of extension portions may be coupled together by a marker coupling portion, whereby the plurality of extension portions are deployed by a single motion advancing the marker coupling portion from the catheter. A marker may be an envelopment marker having a plurality of envelopment marker extensions that each extend along an offset axis from each other. A marker may be a spiral maker that includes a maker extension that spirals around the margin boundary tissue. Two spiral marker extensions may extend in opposing directions to form a double helix maker to define the volume and boundary of the margin tissue.

A marker may be a phase change marker, such as a liquid that becomes a solid upon reaction. The phase change marker may be Ethyl cyanoacrylate (ECA), a cyanoacrylate ester, which is an ethyl ester of 2-cyano-acrylic acid. This adhesive reacts with water to solidify and may effectively bond to tissue upon deposition from a marker extension to mark the margin tissue boundary. A phase change marker may be a two-part phase change marker, such as a two-part adhesive or epoxy, wherein a pair of marker extension has two separate conduits, each delivering one of the two parts of the two-part phase change marker for reaction along the margin tissue boundary. These phase change markers may include a radiopaque material, such as metal particles or radioactive component.

The marker extensions may be configured to extend axially from the catheter to deposit a distal and/or proximal marker configured at the distal boundary of the margin tissue and proximal boundary of the margin tissue, respectively. The marker extensions may extend radially outward from the distal end opening of the catheter and may be directed by a guide head. A first marker may be advanced by the marker extension radially outward to deposit a marker along a first axis of the margin tissue boundary and then a second marker may be deposited along a second axis of the margin tissue boundary. The marker extension may be configured to rotate within the catheter to enable deposition of markers in multiple axes about the margin tissue boundary. The first marker may be deposited and then the marker extension may be rotated, such as 90 degrees, to advance the second marker at said 90-degree radial offset. This process may be repeated four times to deposit markers at substantially each of four radial quadrants, or within about 10 degrees of 90 degree offset. The marker extension may be configured to rotate a fixed amount or degree within the catheter to ensure deposition of markers in a described axis about the tumor.

A new maker extension may be advanced through the catheter for each new marker to be deposited, or a single marker extension may deposit two or more markers. A plurality of phase change markers or seed markers, for example, may be deposited from a single marker extension. In the case of the phase change marker, a surgeon may inject the phase change material a plurality of times from a single marker extension. Also, a plurality of markers may be configured within a single marker extension and a marker plunger may extend within the marker extension to enable pushing a single marker, such as a seed marker, from the distal end of the marker extension. An interference feature may require a force on the marker plunger to deflect the interference feature for depositing a seed marker from the marker extension. An interference feature may be a protrusion into a conduit of the marker extension.

A marker extension may be a shape memory material, such as nitinol and upon deployment from the distal end of the catheter, the shape memory marker extension may extend radially outward from the catheter, or catheter axis. One or more shape memory marker extensions may be advance from the catheter is succession of a plurality of shape memory marker extension may be extended from the catheter at one time. A plurality of marker extensions may include two maker extensions to deposit markers opposite each other along the margin tissue boundary or substantially 180 degrees (within 10 degrees of 180 degrees) offset from each other. A plurality of marker extensions may include three maker extensions to deposit markers along the margin tissue boundary substantially 120 degrees (within 10 degrees of 120 degrees) offset from each other. A plurality of marker extensions may include four maker extensions to deposit markers along the margin tissue boundary substantially 90 degrees (within 10 degrees of 90 degrees) offset from each other or to define quadrants of the margin tissue boundary.

The marker extension may be guided radially outward from the catheter by a guide head. The guide head may have a radial guide that forces the marker extension to extend radially outward from the catheter when advancing the marker extension from the distal end of the catheter. A guide head may be configured to rotate with respect to the catheter to enable deposition of markers an offset radial degree from each. Again, a first marker may be advance radially outward from the catheter and guided by the guide head to a first radial position and deposited along the margin tissue boundary. The marker extension may then be retracted. The guide head may then be rotated an offset radial degree and the same or a new marker extension may be advanced from the distal end of the catheter and guided by the guide head to deposit a second marker at said radial offset degree from the first marker. This process may be repeated until an effective number of markers are deposited to produce a multi-axis set of markers along the margin tissue boundary. Alternatively, the guide head may be configured to guide a plurality of marker extension radially outward at the same time. A guide head may have a plurality of radial guide apertures to direct marker extensions at radial offset degrees from each other, such as about 180 degrees, 120 degrees or 90 degrees from each other, or within about 10 degrees of each other. A guide head may also have an axial aperture to enable advancement of a radial marker extension from the guide head. In an exemplary embodiment, the guide head includes a plurality of radial guide apertures and an axial aperture to enable depositing a distal marker and a plurality of radial markers in a single advancement of the marker extensions. These plurality of marker extensions may have a length that is preset for a prescribed margin tissue size or volume around the tumor. Depositing markers in this way ensures that an effective amount of margin tissue will be marked for excision.

Radial markers may be advanced from the catheter to produce radial markers configured along the center radial axis, or centrally between the distal margin boundary and proximal margin boundary. Radial markers may also be deposited at some offset axial distance between the central radial axis and one of the distal end or proximal end of the margin tissue. Note that the length of advancement of the marker extensions may be changed depending on the position of the distal end of the catheter along the catheter axis.

A marker may include an anchor portion that is configured along the margin tissue boundary and an extension portion that extends from the anchor portion, such as radially inward toward the tumor. The anchor portion may include a radiopaque material while the extension portion may not and may be a surgical guide, such as a line that guides the surgeon to the margin tissue anchor portion. An anchor portion may be a shape memory wire that takes a convoluted shape upon advancement from the marker extension, such as a zig-zag shape, or spiral shape to fix the marker within the tissue to prevent migration within the tissue. An anchor marker may be configured to rotate upon deployment or release from the marker extension and this rotation may also prevent migration of the marker along the aperture in the tissue formed by the marker extension.

A marker may be an envelopment marker having an envelopment marker extension that extends along the margin boundary tissue, such as at least 90 degrees, and may extend in a radius of curvature about the margin tissue boundary. The envelopment marker extensions may be shape memory material that is preconfigured to extend in a shape to define a margin tissue boundary and may be preconfigured to extend in a curve or radius of curvature to define a spherical margin tissue for excision. A plurality of envelopment markers may be deposited or deployed at offset axis from each other to produce an envelopment marker arrangement. In an exemplary embodiment three envelopment marker extensions extend at substantially 120 degrees (within 10% of 120 degrees) offset from each other about a legion or a catheter axis. In an exemplary embodiment four envelopment marker extensions extend at substantially 90 degrees (within 10% of 90 degrees) offset from each other about a legion or a catheter axis. In an exemplary embodiment, a plurality of envelopment marker extensions are coupled together by a marker coupling portion. The catheter may be advanced to locate the distal end proximal to the proximal margin tissue boundary and then one or more envelopment marker extensions may be advanced from the catheter to extend along the margin tissue boundary. A trace line may be coupled to a marker extension or to a marker coupling portion. The trace line may lead to the from the marker coupling portion out toward the skin and may protrude from the skin to guide the surgeon to the marker coupling portion. A trace line may be soft material, such as a suture and may pose no risk to damaging the surgeon's gloves.

A preferred marker is an envelopment marker having a plurality of envelopment marker extensions coupled to a marker coupling portion, wherein a single advancement from the catheter by the marker deploys each of the plurality of envelopment marker extensions along a different axis of the margin tissue boundary. An envelopment marker may be deployed from the proximal margin tissue boundary and therefore may prevent any disruption of the tumor. However, an envelopment marker may be deployed from the distal margin tissue boundary whereby the envelopment marker extensions extend back toward the proximal margin tissue boundary.

An exemplary envelopment marker is a spiral envelopment marker that spirals about a length axis from the proximal margin tissue boundary to a distal margin tissue boundary or around a catheter axis. The spiral envelopment marker may make a number or revolutions (360 degree) about the length axis from the proximal margin tissue to the distal margin tissue, such one revolution or more, about two revolutions or more, about three revolutions or more, about four revolutions or more and any range between and including the values provided. An exemplary spiral envelopment marker may include two separate spiral envelopment markers that spiral about the margin tissue in opposing directions, one clockwise, one counterclockwise. The two spiral envelopment markers may form a double helix configuration about the tumor. The spiral envelopment markers may be shape memory material that advances from the catheter to spiral about the tumor. The spiral envelopment markers may spiral to form a spherical shape about the tumor, wherein the radius of curvature proximal to the proximal and distal end of the margin tissue is smaller than the radius of curvature along the center portion between the proximal and distal margin tissue boundary.

Markers configured in multiple axes about a tumor, as used herein, means that two or more markers are configured in an offset distance from each other about the tumor, wherein a first marker is configured at a first axis and a second marker is configured an offset degree about the tumor from the first marker. This offset degree may depend on the number of markers used and may be about 45 degrees or more, about 60 degrees or more, about 90 degrees or more, about 120 degrees or more, about 180 degrees or more and any range between and including the offset degree provided. In an exemplary embodiment, three markers are placed substantially uniformly about the tumor, wherein each is about 120 degrees offset from the adjacent markers, or within about 10 degrees or 120 degrees. In another exemplary embodiment, four markers are placed substantially uniformly about the tumor, wherein each is about 90 degrees offset from the adjacent markers, or within about 10 degrees or 120 degrees.

Margin is defined as the amount of healthy tissue around a tumor. The amount or size of the margin is determined by the physician, scientific literature, tumor type, location, stage and current guidelines. Commonly use margins are 5 mm, 10 mm, and 20 mm from the center of an identified mass, legion or cancerous tumor. A tumor, as used herein, may refer generically to a mass, legion or a cancerous tumor.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

FIG. 10 shows a perspective view of a tumor-excision marker system configured to mark the margin tissue around a tumor indicated for excision and a catheter inserted into the margin tissue to deploy a shape-memory wire radiopaque marker at the distal boundary of the margin tissue.

FIG. 11 shows a perspective view of the tumor and the margin tissue shown in FIG. 10 with the shape-memory wire radiopaque markers deployed to indicate the margin tissue for excision, wherein the shape-memory wire has an anchor portion and an extension portion, wherein the anchor portion is configured at the boundary of the margin tissue and the extension extends in toward the center of the margin tissue or toward the tumor.

FIG. 12 shows a cross-sectional view of the tumor and margin tissue shown in FIG. 11 along a centerline axis, wherein there are four shape-memory wire radiopaque markers configured to indicate the margin tissue boundary and location of the tumor with respect to the boundary.

FIG. 13 shows a perspective view of a tumor-excision marker system configured to mark the margin tissue around a tumor indicated for excision and a catheter inserted into the margin tissue to deploy a discrete marker at the distal boundary of the margin tissue.

FIG. 14 shows a perspective view of the tumor and the margin tissue shown in FIG. 10 with the seed marker deployed to indicate the margin tissue for excision.

FIG. 15 shows a cross-sectional view of the tumor and margin tissue shown in FIG. 14 along a centerline axis, wherein there are four seed markers configured to indicate the margin tissue boundary and location of the tumor with respect to the boundary.

FIG. 17 shows a perspective view of the tumor and the margin tissue shown in FIG. 16 with the envelopment marker deployed to indicate the margin tissue for excision, wherein the envelopment marker has a marker coupling portion from which each of the plurality of envelopment marker extensions extend from.

FIG. 19 shows a perspective view of the tumor and the margin tissue shown in FIG. 18 with the envelopment marker deployed to indicate the margin tissue for excision, wherein the envelopment marker has a marker coupling portion from which each of the plurality of envelopment marker extensions extend from.

FIG. 22 shows a perspective view of a tumor-excision marker system configured to mark the margin tissue around a tumor indicated for excision and a catheter inserted into the margin tissue to deploy an anchor marker to define the distal margin tissue.

FIG. 23 shows a perspective view of the tumor and the margin tissue shown in FIG. 22 with the anchor markers deployed to indicate the margin tissue for excision.

FIG. 24 shows a cross-sectional view of the tumor and margin tissue shown in FIG. 23 along a centerline axis, wherein there are four anchor markers configured to indicate the margin tissue boundary and location of the tumor with respect to the boundary.

Figure 1:
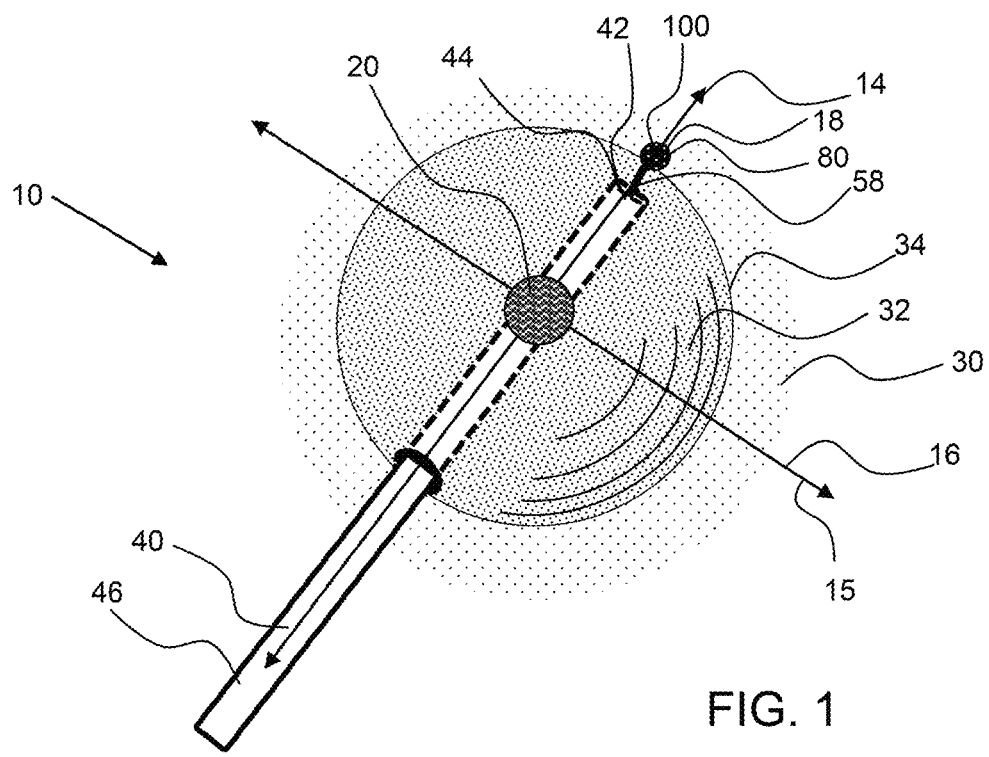
FIG. 1 shows a perspective view of a tumor-excision marker system configured to mark the margin tissue around a tumor indicated for excision and a catheter inserted into the margin tissue to place a radiopaque marker at the distal boundary of the margin tissue.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to be understood that where possible, features and components from one figure may be included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations, and improvements of the described embodiments, will occur to those skilled in the art and all such alternate embodiments, combinations, modifications, improvements are within the scope of the present invention.

As shown throughout the figures, tissue 30 is configured around the margin tissue 32 and the margin tissue extends around the tumor 20. The margin tissue has a margin tissue boundary 34.

Referring now to FIGS. 1 to 7, an exemplary multi-axis tumor marker system 10 is configured to mark the margin tissue 32 in multiple axes around a tumor 20 indicated for excision by placing markers, such as radiopaque markers 18, along the margin tissue boundary 34 and optionally within the margin tissue. Tissue 30 around the margin tissue 32 is shown. As shown in FIG. 1, the multi-axis tumor marker system 10 utilizes a catheter 40 to locate a radiopaque marker 18 at the distal boundary of the margin tissue. An axial marker-extension 58 extends through the catheter tube 46 and out of the distal end opening 44 of the catheter along the catheter axis 14, that extends along the length of the catheter. The radiopaque markers 18 may be injected out of the axial marker-extension and may be a phase change marker 100, a liquid that solidifies or adheres to the tissue after injection into the tissue. The phase change marker 100 may include cyanoacrylate adhesive that reacts with moisture to cure and become solid. The distal end marker 80 is configured to mark the distal margin tissue 37. The radiopaque marker 18 may be a phase change marker 100 that changes from a liquid phase to a solid phase and one or more markers may be deposited by a single marker extension 50.

Figure 2:
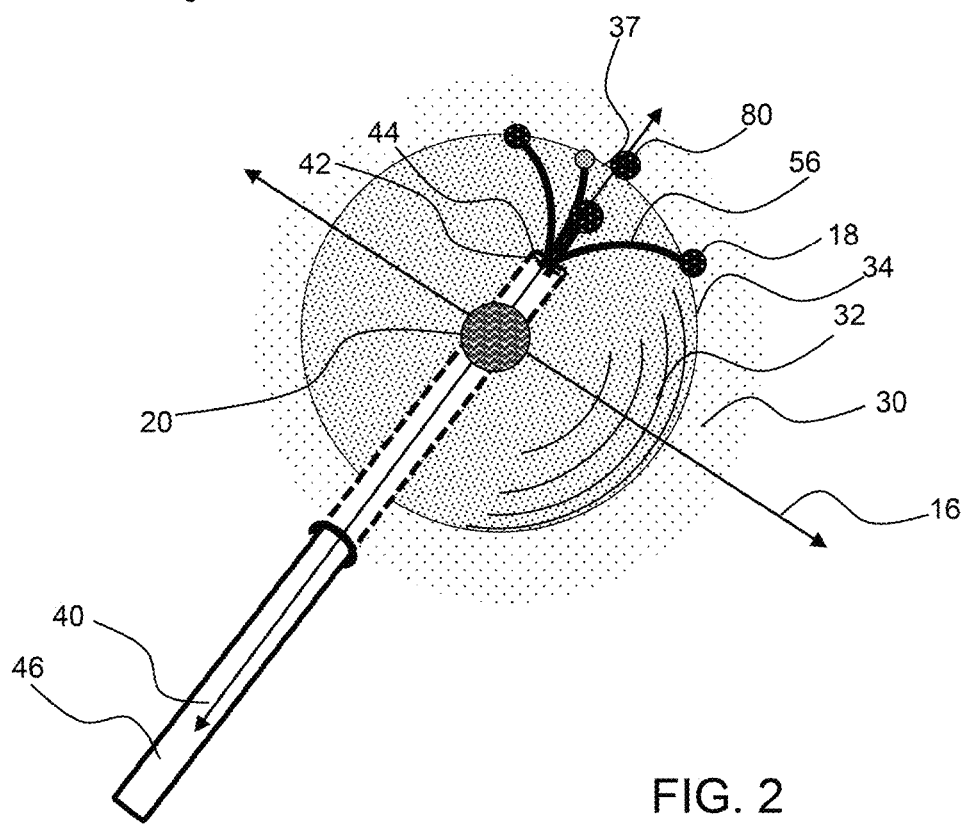
FIG. 2 shows a perspective view of the tumor-excision marker system shown in FIG. 1, now with the catheter withdrawn and radial marker-extensions extending from the catheter to place radiopaque markers radially about the boundary of the margin tissue.

As shown in FIG. 2, the multi-axis tumor marker system 10 utilizes a plurality of radial marker-extensions 56 extending from the catheter distal end opening 44 to locate radiopaque markers 18 radially about the margin tissue boundary 34. The radial marker-extensions may be deflected by a guide head (shown in FIGS. 8 and 9) that may be configured over the distal end of the catheter. The marker-extension may be a shape-memory radial marker-extensions that extend radially outward when advance out of the distal end of the catheter with or without a guide head.

In an exemplary embodiment, a marker extension extends within a catheter and is configured to be guided by a guide head or guide conduit within the catheter that is configured for rotational adjustment within the catheter, whereby the catheter can be advanced to a desired location and a first marker-extension can be deployed through the catheter and guided in a first axis radially outward from the distal end of the catheter to a margin tissue boundary, whereby a marker is deposited. The marker-extension can then be retracted and the guide head can be rotated such that a second marker-extension is directed radially outward in a second axis from the distal end of the catheter. This process may be repeated to mark a plurality of axis about the margin tissue boundary.

Figure 3:
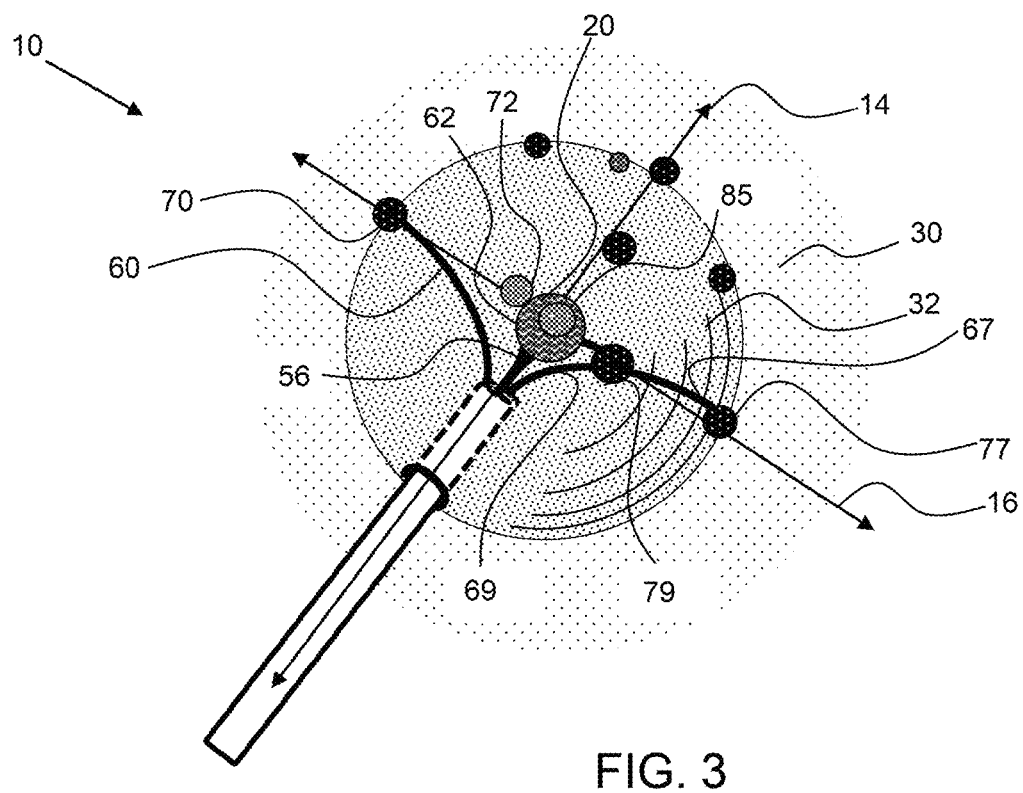
FIG. 3 shows a perspective view of the tumor-excision marker system shown in FIG. 2, now with the catheter withdrawn from the position shown in FIG. 2 and the axial marker-extension placing a center radiopaque marker in the center of the margin tissue, and radial marker-extensions extending from the catheter to place radiopaque markers radially about a centerline radial boundary of the margin tissue.

As shown in FIG. 3, the multi-axis tumor marker system 10 is configured to deposit radiopaque markers radially about a central axis of the margin tissue 32, wherein four marker-extension extend radially outward from the catheter. As shown, these four radially extending marker-extensions are configured about 90 degrees offset from each other. As shown a 0-degree marker-extension 60 is configured to deposit a 0-degree marker 70, a 90-degree marker-extension 62 is configured to deposit a 90-degree marker 72, a 180-degree marker-extension 67 is configured to deposit a 180-degree marker 77 and a 270-degree marker-extension 69 is configured to deposit a 270-degree marker 79. Also note that an axial marker-extension 58 may be configured to place a center marker 85 in the center of the margin tissue 32.

Figure 4:
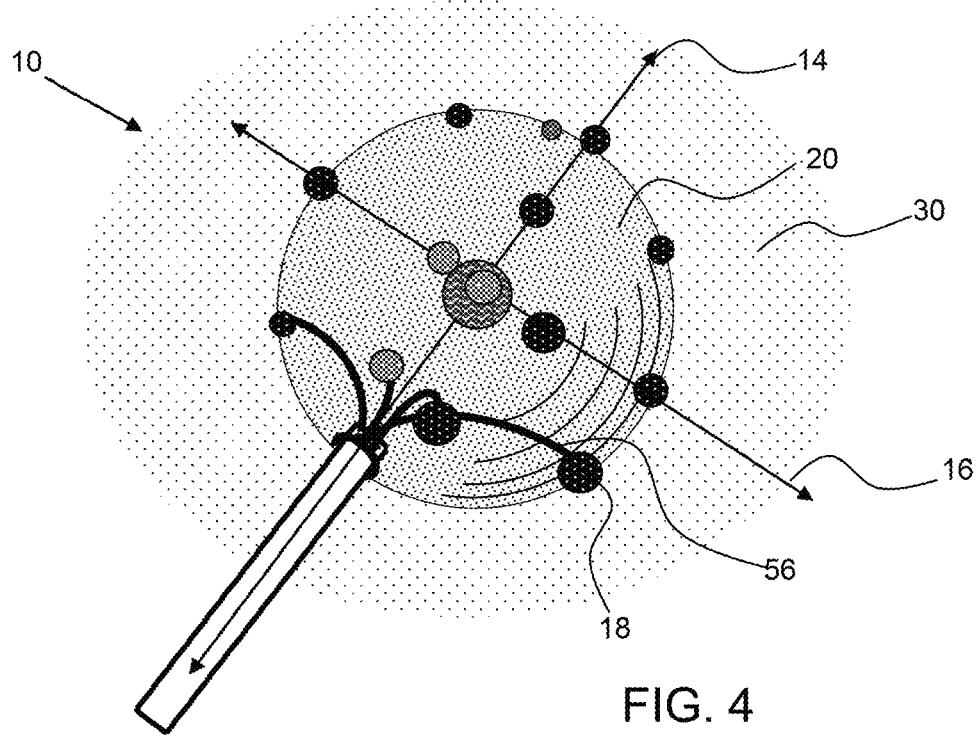
FIG. 4 shows a perspective view of the tumor-excision marker system shown in FIG. 3, now with the catheter withdrawn from the position shown in FIG. 3 and radial marker-extensions extending from the catheter to place radiopaque markers radially about the boundary of the margin tissue.

As shown in FIG. 4, the multi-axis tumor marker system 10 shown in FIG. 3, is now configured with the catheter withdrawn from the position shown in FIG. 3 and radial marker-extensions 56 extending from the catheter to place radiopaque markers radially about the boundary of the margin tissue.

Figure 5:
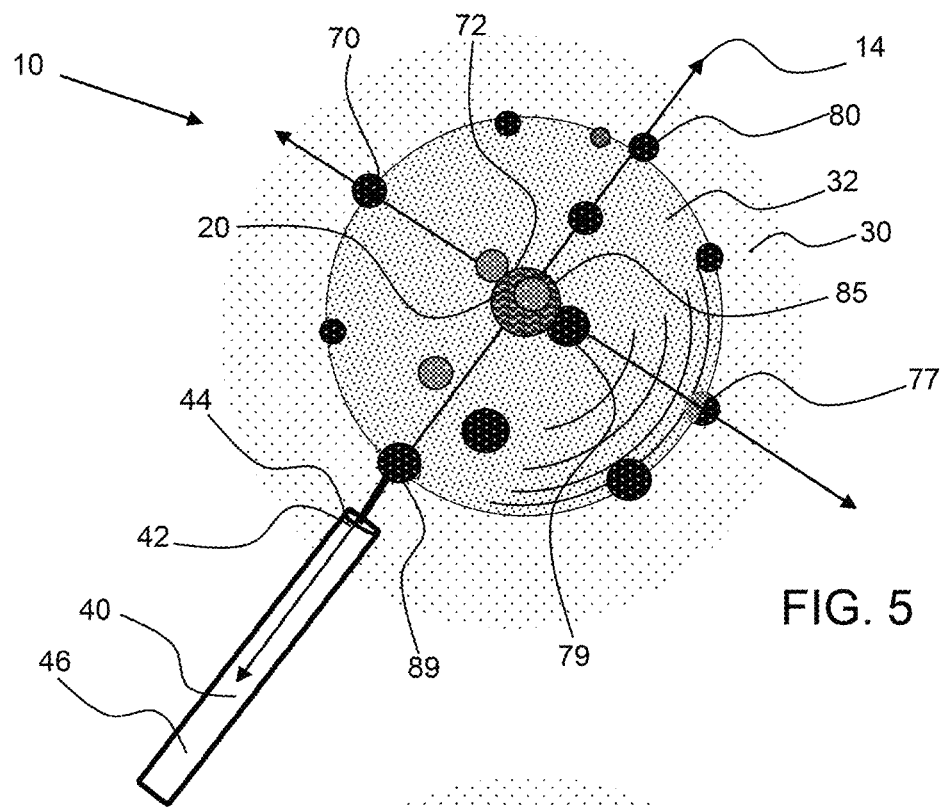
FIG. 5 shows a perspective view of the tumor-excision marker system shown in FIG. 4, now with the catheter withdrawn from the position shown in FIG. 4 and the axial marker-extension extending from the catheter to place radiopaque markers radially along the proximal boundary of the margin tissue.

As shown in FIG. 5, the multi-axis tumor marker system 10 shown in FIG. 4, is now configured with the catheter withdrawn from the position shown in FIG. 4 and the axial marker-extension 58 extending from the catheter to place radiopaque markers radially along the proximal boundary of the margin tissue, a proximal marker 89. The margin tissue boundary 34 has a plurality of markers defining the boundary including a distal marker 80, proximal marker 89, center marker 85 and a plurality of radial markers.

Figure 6:
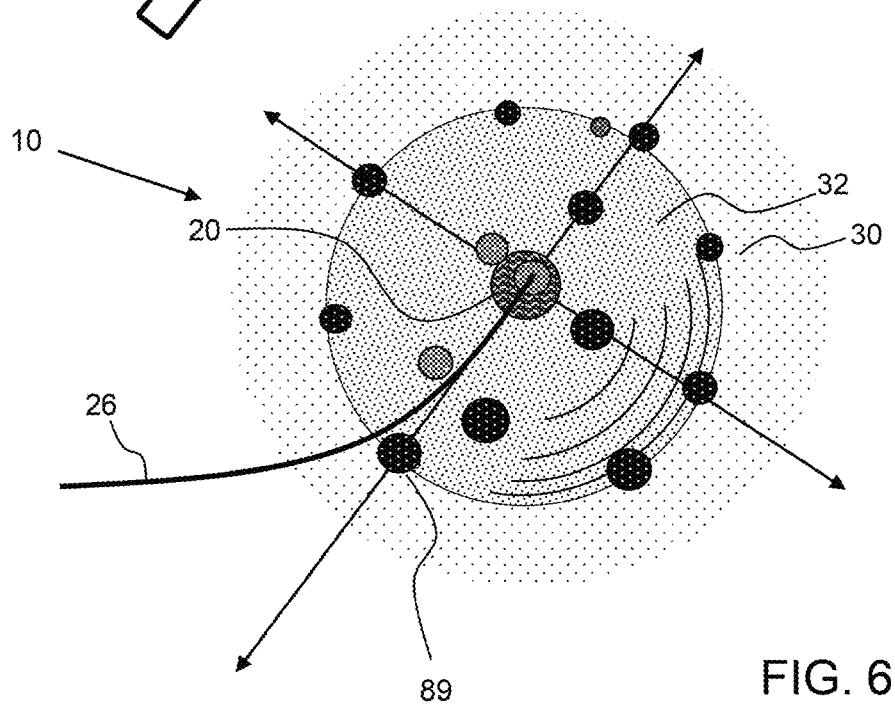
FIG. 6 shows a perspective view of the tumor and radiopaque markers configured about the boundary of the margin tissue and a center radiopaque marker configured centrally within the margin tissue.

As shown in FIG. 6, the margin tissue 32 around a tumor 20 is marked with radiopaque markers 18 configured about the boundary of the margin tissue and a trace line 26 extends out from the margin tissue to guide a surgeon to the excision region.

Figure 7:
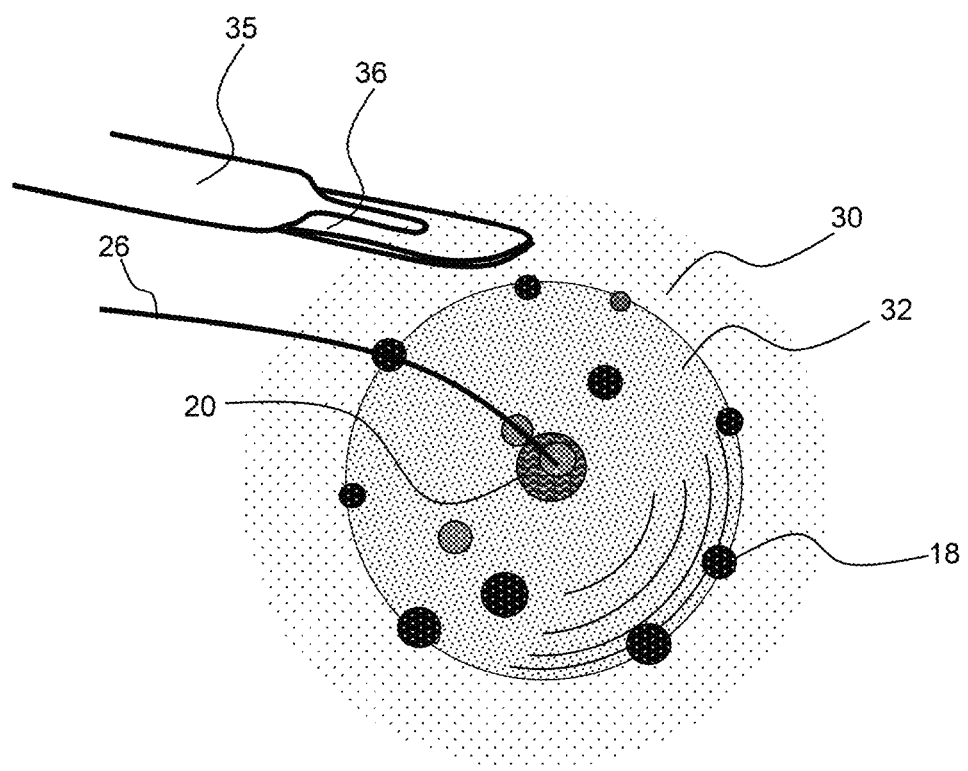
FIG. 7 shows a scalpel being used to excise the margin tissue and the radiopaque markers around the tumor.

As shown in FIG. 7, a tissue excision implement 35, such as a scalpel 36 is being used to excise the margin tissue 32 and the radiopaque markers 18 around the tumor 20.

Figure 8:
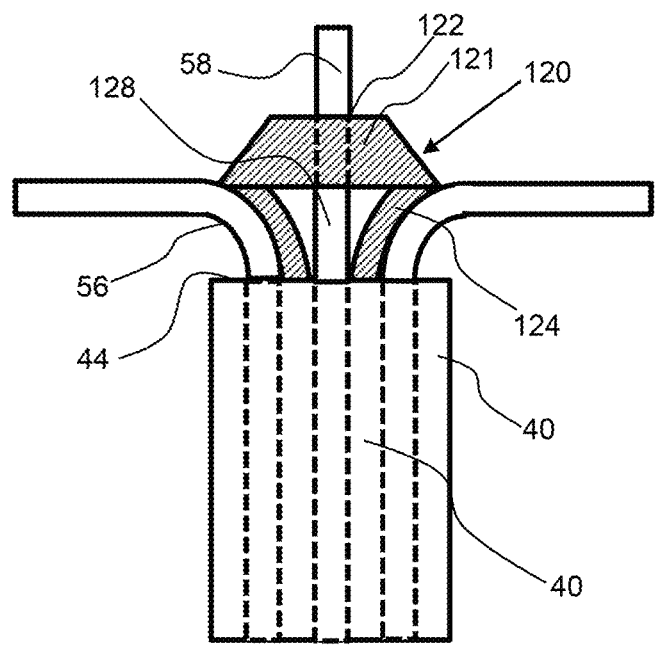
FIG. 8 shows a top view of a radiopaque-marker catheter having an extension guide head with an axial opening for guiding the axial marker-extension out axial from the catheter and four radial marker openings configured to force the radial markers to turn radially outward from the guide head.
Figure 9:
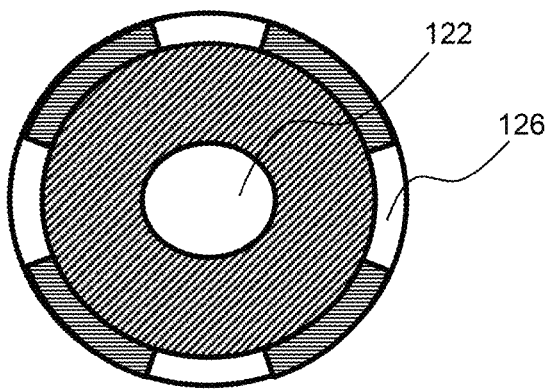
FIG. 9 shows a side view of the radiopaque-marker catheter shown in FIG. 8, with the axial marker-extension extending through the axial opening in the guide head and radial marker-extensions extending radially from radial marker opening and being deflected by the guide head.

Referring now to FIGS. 8 and 9, a radiopaque-marker catheter 40 has a guide head 120 with an axial opening 122 for guiding the axial marker-extension 58 out axial from the catheter and four radial marker openings 126 with radial guides 124 configured to force the radial marker-extensions to turn radially outward from the guide head. The radial guide is a surface of the guide head that is curved to turn the marker-extension out radially. A marker-extension may be a shape memory material and may naturally want to turn radially outward when deployed from the restraining distal end 42 of the catheter. The guide head shown may enable four axis of radial deployment and marking at one time, however, this may require a larger catheter which may not be suitable for all conditions. A guide head 120 may only have one, two or three radial marker openings 126. In an exemplary embodiment, a guide head has a single or two radial marker openings and the guide head 120 may be configured to be turned with respect to the catheter, wherein a first marker or markers are deposited along the margin tissue boundary and then the guide head is rotated to position the radial marker opening in new offset axis for a second deployment and deposition of markers on the margin tissue boundary. The guide head 120 may be coupled with a guide head actuator extension 128 extending through the catheter to enable rotation of the guide head by the clinician on the proximal end of the catheter. The guide head may be coupled to a concentric sheath or tube extending within the catheter, for example.

Referring now to FIGS. 10 to 12, a multi-axis tumor marker system 10 is configured to mark the margin tissue around a tumor 20 indicated for excision. As shown in FIG. 10, a catheter 40 is inserted into the margin tissue, to the distal margin tissue 37, to deploy a shape-memory wire marker 90 at the distal boundary of the margin tissue 32 to produce a distal marker 80. The shape memory wire marker is a convoluted marker 91 having bends to better enable fixation and reduce the likelihood of migration of the marker. The convoluted marker may be restrained by the catheter 40 or the marker extension 50 and then take a convoluted shape when the convoluted marker is deployed from the distal end opening 44 of the catheter 40. This convoluted marker 91 produced an anchor portion 92 of the marker and, as shown in FIGS. 11 and 12, the marker has an extension portion 94 that extends radially inward toward the tumor 20. The anchor portion 92 of the marker may be radiopaque and the extension portion may also be radiopaque or may be a suture, wire, or plastic line.

As shown in FIG. 11, six shape memory wire markers 90 are configured to define and mark the boundary of the margin tissue 32. Each of the six shape memory wire markers 90 have an anchor portion 92 configured along the margin tissue boundary 34 and an extension portion 94 extending radially inward toward the tumor 20. Each shape memory wire markers 90 is configured on an axis to produce a multi-axis marker arrangement to better ensure complete removal of the prescribed margin tissue. The shape memory wire markers 90', 90", 90"', 90"", extending radially from a central position between the distal marker 80 and proximal marker 89 may be deployed from a radial marker-extension as shown best in FIG. 3. A trace line 26 may extend from the shape memory wire marker arrangement to enable a surgeon to follow the trace line to the margin tissue for excision.

FIG. 12 shows the multi-axis arrangement of the shape memory wire markers 90.

Referring now to FIGS. 13 to 15, a multi-axis tumor marker system 10 is configured to mark the margin tissue around a tumor 20 indicated for excision. As shown in FIG. 13, a catheter 40 is inserted into the margin tissue 32, to the distal margin tissue 37, to deploy a distal marker 80, a seed marker 110 at the distal boundary of the margin tissue. The seed marker is a discrete physical marker that may be radiopaque and may be metal or include a radioactive component to enable location during x-ray imaging. The seed marker may be deposited by the catheter 40 or the marker extension 50 from the distal end opening 44 of the catheter. The seed markers 110 extending radially from a central position between the distal marker 80 and proximal marker 89 may be deployed from a radial marker-extension as shown best in FIG. 3. Note that the seed markers configured around the central radial axis 15 may be offset from each other 90 degrees as shown about the central perimeter of the margin tissue boundary 34. As shown in FIG. 15, a trace line 26 extends from the seed marker arrangement to enable a surgeon to follow the trace line to the margin tissue for excision. As shown in FIG. 14, markers are positioned along the length axis, or catheter axis 14 and the center radial axis 15, extending radially out or orthogonal to the length or catheter axis centrally between the distal margin tissue 37 and proximal margin tissue 39. A radial axis 16 is an axis orthogonal to the catheter or length axis that may be anywhere along the margin tissue.

Figure 16:
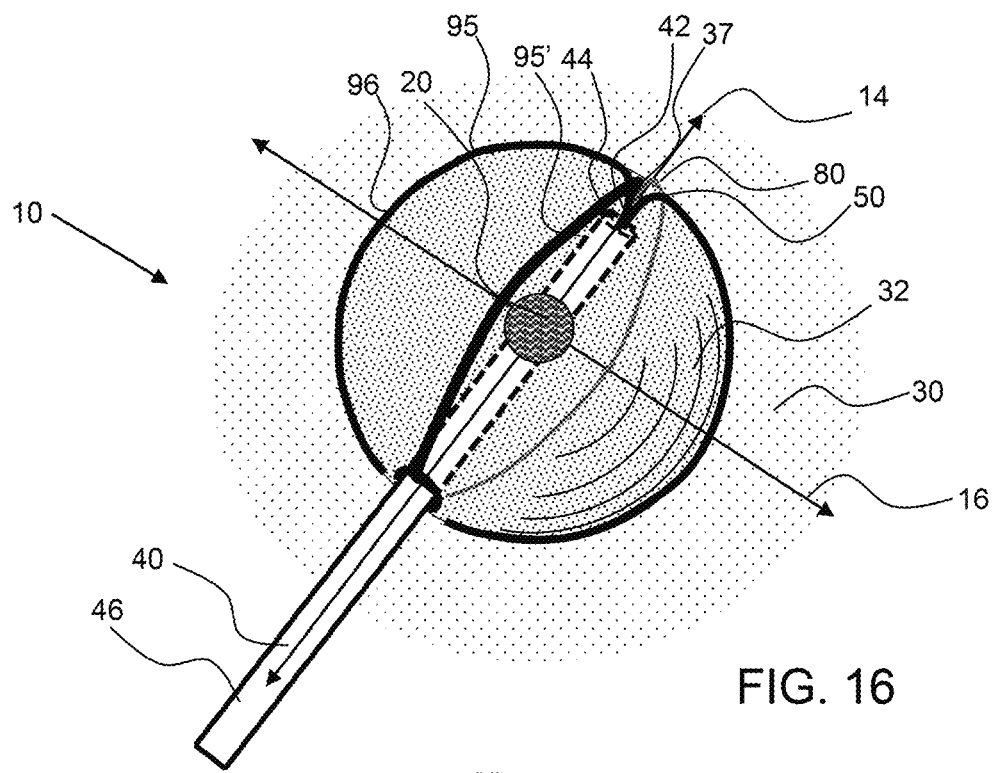
FIG. 16 shows a perspective view of a tumor-excision marker system configured to mark the margin tissue around a tumor indicated for excision and a catheter inserted into the margin tissue to deploy an envelopment marker that has a plurality of envelopment marker extensions that extend along a radius of curvature to define a boundary of the margin tissue for excision.
Figure 19:
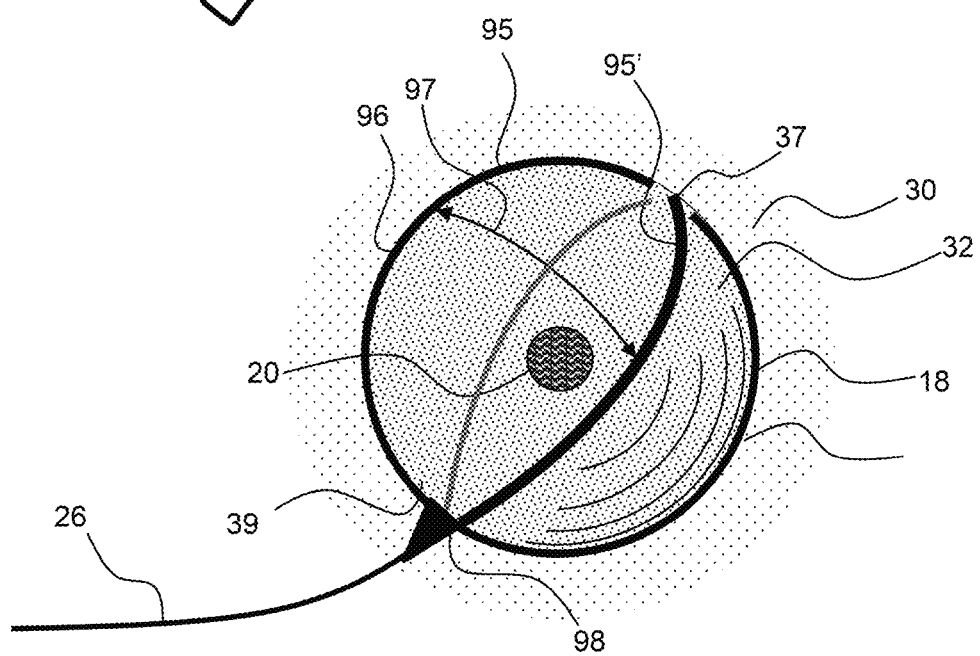

Referring now to FIGS. 16 and 19, a multi-axis tumor marker system 10 may employ an envelopment marker 96 configured to mark the margin tissue 32 around a tumor 20 indicated for excision. As shown in FIG. 16, a catheter 40 is inserted into the margin tissue 32 to deploy an envelopment marker 96 having a plurality of envelopment wire marker extensions 95, 95' that may be a shape-memory wire that extends from the distal end 44 of the catheter 40 or marker extension 50 along a curved boundary of the margin tissue. The envelopment wire marker extensions 95 may extend back from the distal end of the catheter 42 and distal margin tissue 37 toward the proximal end of the catheter or proximal margin tissue 39 along a radius of curvature, thereby defining a multi-axis volume of margin tissue 32 for excision. As shown, there are four envelopment wire marker extensions and they are configured an offset radial angle 97 of approximately 90 degrees to define the spherical volume of margin tissue for excision, as shown in FIG. 19. Put another way, each of the shape memory wire markers extend along a separate axis to define the volume, such as a spherical volume for excision.

Figure 17:
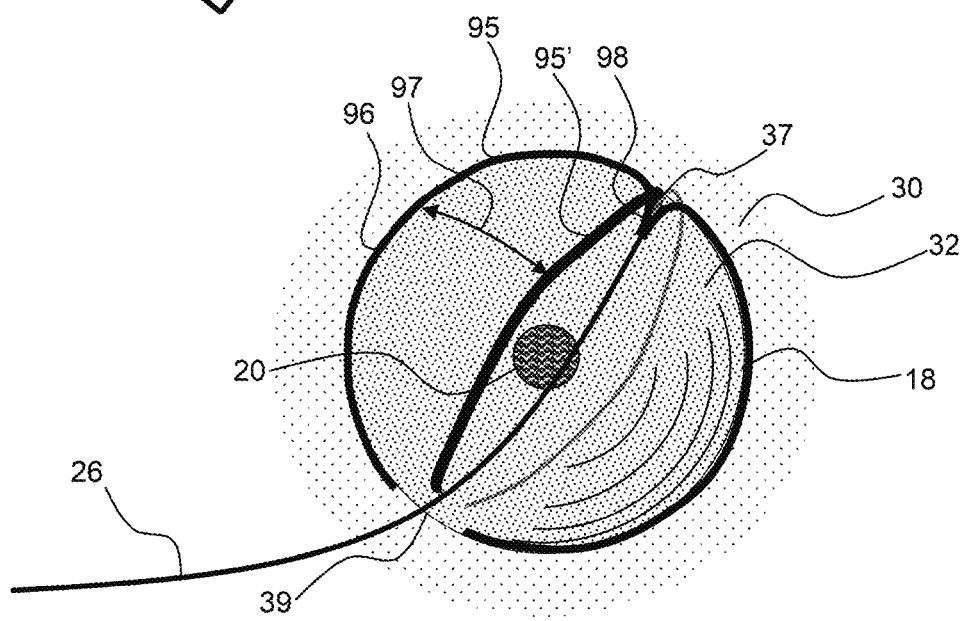

As shown in FIG. 17, each of the envelopment wire marker extensions 95, 95' of the envelopment marker 96 are coupled together by a marker coupling portion 98 configured near the distal margin tissue 37. Also, a trace line 26 extends from the envelopment marker 96, such as from the marker coupling portion 98, away from the margin tissue 32. The trace line may extend proximal to or out from the skin of the patient to provide a surgeon a guide to locate the tumor 20 and the envelopment marker 96 for excising the margin tissue around the legion. The trace line may be a suture or other non-radiopaque material.

Figure 18:
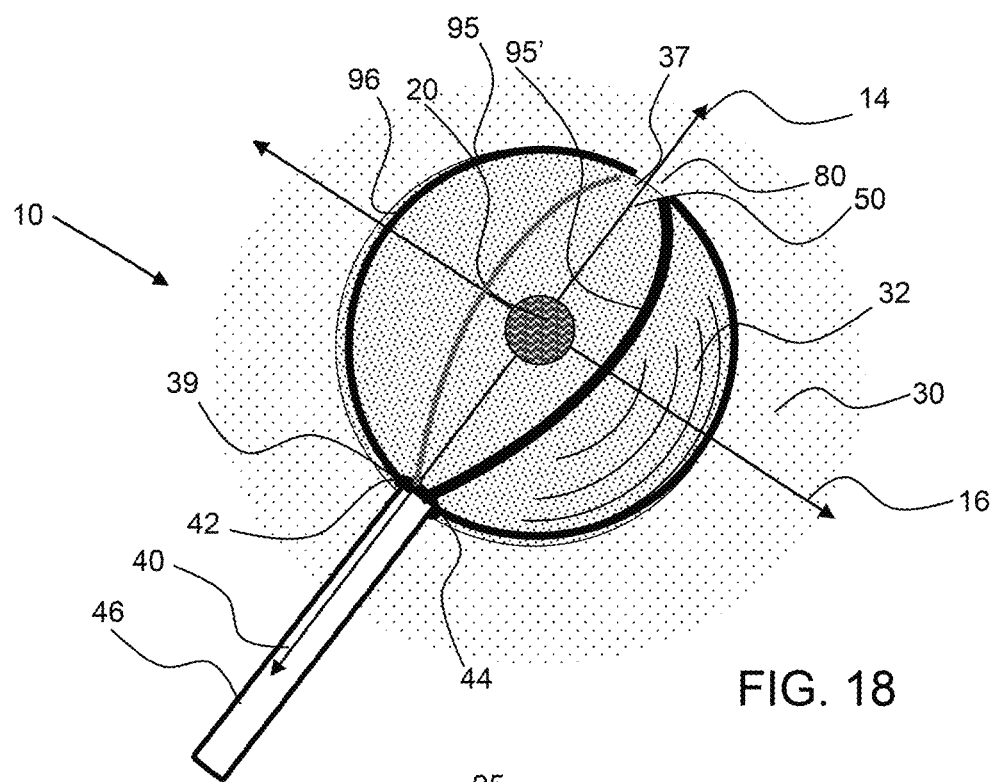
FIG. 18 shows a perspective view of a tumor-excision marker system configured to mark the margin tissue around a tumor indicated for excision and a catheter inserted to the proximal margin tissue to deploy an envelopment marker that has a plurality of envelopment marker extensions that extend along a radius of curvature toward the distal margin tissue to define a boundary of the margin tissue for excision.

As shown in FIGS. 18 and 19, a catheter 40 is inserted to the proximal margin tissue 39 to deploy an envelopment marker 96 having a plurality of envelopment wire marker extensions 95, 95' that may be a shape-memory wire that extends from the distal end opening 44 of the catheter 40 or marker extension 50 along a curved boundary of the margin tissue to the distal margin tissue 37. The envelopment wire marker extensions 95 may extend out from the distal end of the catheter 42 and proximal margin tissue 37 toward the distal margin tissue 37 along a radius of curvature, thereby defining a multi-axis volume of margin tissue 32 for excision. As shown, there are four envelopment wire marker extensions and they are configured an offset radial angle 97 of approximately 90 degrees to define the spherical volume of margin tissue for excision. The catheter axis 14 is shown and is the axis of the elongated axis of the catheter.

Figure 20:
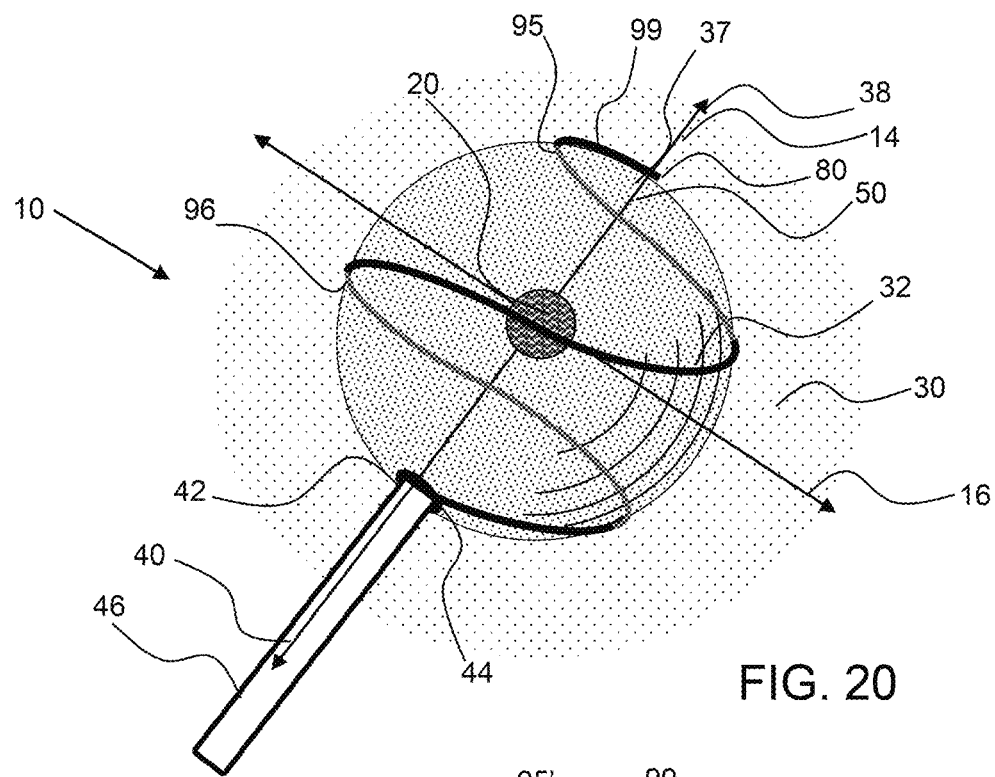
FIG. 20 shows a perspective view of a tumor-excision marker system configured to mark the margin tissue around a tumor indicated for excision and a catheter inserted into the margin tissue to deploy a spiral envelopment marker that has an envelopment marker extensions that spirals around the tumor to define a boundary of the margin tissue for excision.
Figure 21:
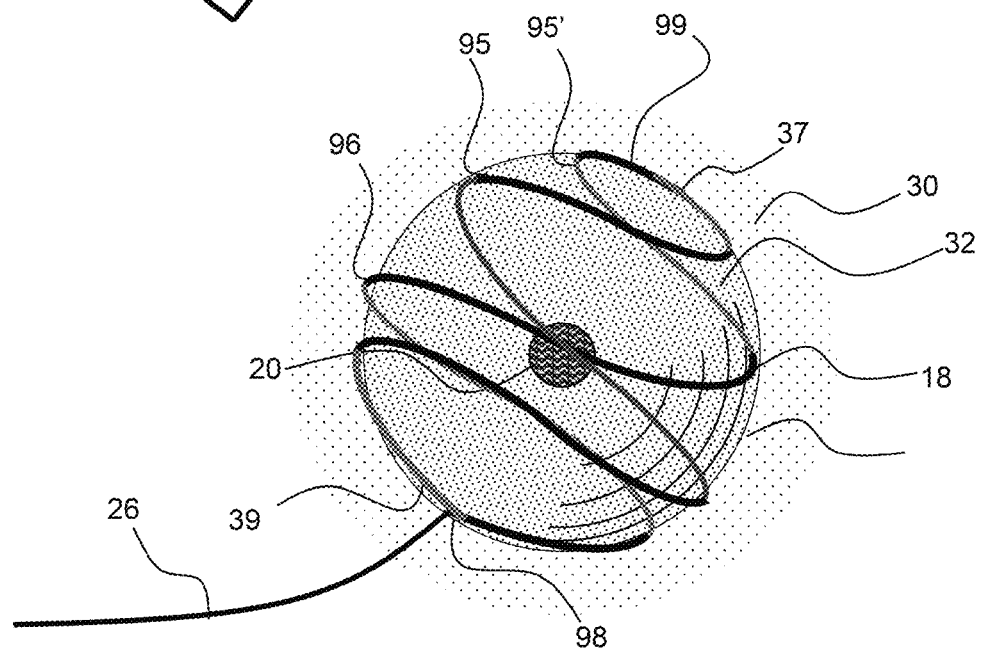
FIG. 21 shows a perspective view of the tumor and the margin tissue shown in FIG. 20 with the spiral envelopment marker deployed to indicate the margin tissue for excision, wherein the spiral envelopment marker has a trace line extending from the marker.

As shown in FIGS. 20 and 21, a catheter 40 is inserted to the proximal margin tissue 39 to deploy an envelopment marker 96, that is a spiral envelopment marker 99 having a plurality of envelopment wire marker extensions 95, 95' that may be a shape-memory wire that extends from the distal end opening 44 of the catheter 40 or marker extension 50 from the proximal margin tissue 39, along a curved boundary of the margin tissue to the distal margin tissue 37. The spiral envelopment marker may spiral about a length axis 38 of the margin tissue, the axis from the distal margin tissue 37 to the proximal margin tissue 39. The envelopment wire marker extensions 95 may extend out from the distal end of the catheter 42 and proximal margin tissue 37 toward the distal margin tissue 37 along a radius of curvature, thereby defining a multi-axis volume of margin tissue 32 for excision. As shown in FIG. 21, there are two envelopment wire marker extensions and they are configured an to extend in opposing direction to produce a double helix envelopment marker.

Referring now to FIGS. 22 to 24, an exemplary multi-axis tumor marker system 10 has anchor markers 112 that may be rotational anchor markers 114 configured to extend out from the catheter 40 or marker extension 50 and then rotate to promote fixation in the tissue, as indicated by the bold curved arrow in FIG. 22. The anchor markers may be elongated anchor markers having a length that is greater than the width by a factor of about 1.5 or more, 2.0 or more, or even 3.0 or more. The length of the anchor marker extends along the catheter 40 and/or marker extension 50 and upon deployment, the anchor marker 112 may rotate such that the length axis is at an offset angle from the length axis of the catheter or maker extension. Preferably the anchor marker rotates to be substantially orthogonal to the catheter axis 14, extending along the length of the catheter, or within about 20 degrees of orthogonal. This rotation of the elongated anchor marker 112 may provide effective fixation in the tissue, wherein the anchor marker does not migrate, along the aperture produced by the catheter or marker extension. Also, a trace line 26 may be coupled to one or more or all of the anchor markers 112 and may extend away from the margin tissue toward the skin or extend out from the skin of the patient to guide the surgeon to the margin tissue for excision.

The anchor markers may be plastic, metal, radiopaque or bioresorbable material and may be made without sharp edges to prevent cutting of the surgeon's glove. A bioresorbable anchor marker may be configured to remain in the patient.

Figure 25:
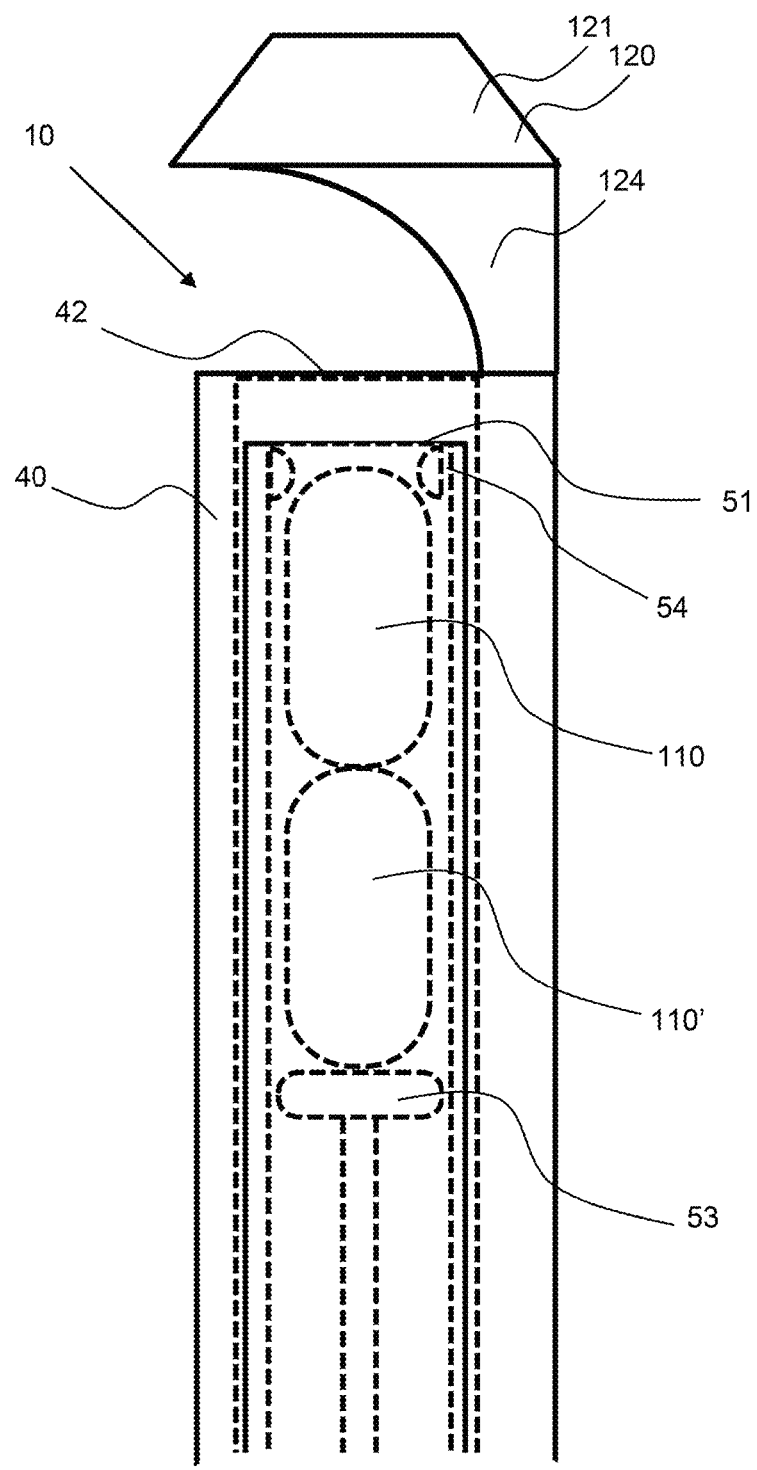
FIG. 25 shows a side view of an exemplary catheter with a radial guide heat and with a marker extension configured therein and having a plurality of seed markers configured to be advanced out of the marker extension conduit by a marker plunger.

As shown in FIG. 25, an exemplary catheter 40 has guide head 120 with a radial guide 124 to advance the marker extension 50 radially outward from the distal end 42 of the catheter. An interference feature 54 is configured on the distal end 51 of the marker extension requiring an overcoming force on the marker plunger 53 to deposit one of the seed markers 110, 110' along a margin tissue boundary. Note that the catheter may be retracted back into the catheter 40 after depositing the first seed marker 110 and then the catheter or guide head 120 may be rotated to enable advancing the marker extension 50 in a second axis radially out for depositing the second seed marker 110' along an offset axis from the first seed marker. The guide head may have a guide head cap 121 that may be tapered.

It will be apparent to those skilled in the art that various modifications, combinations, and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A multi-axis tumor marker system comprising:
   a) a catheter having a proximal and a distal end with a distal end opening;
   b) a marker extension configured to retain a marker and extend from the distal end opening of the catheter for depositing said marker;
   wherein the marker is deposited along multiple axes radially about a tumor to define a boundary of margin tissue for excision;
   wherein the marker extension comprises an axial marker-extension configured to extend axially from the distal end opening of the catheter to deposit said marker along a catheter axis;
   wherein the axial marker-extension is configured to deposit said marker on a distal end of said boundary of said margin tissue to produce a distal marker; and
   a plurality of radial marker-extensions, each extending within the catheter and containing a radial marker;
   wherein each of the plurality of radial marker-extensions is configured to extend radially out from the distal end opening of the catheter when pushed out from said distal end opening; and wherein each of the plurality of radial marker-extensions is configured to deposit said radial marker on a radial boundary of said margin tissue; and wherein a zero degree radial marker-extension of the plurality of radial marker-extensions is configured to extend in a zero degree radial direction from the distal end opening and wherein a 180 degree radial marker-extension of the plurality of radial marker-extensions is configured to extend substantially 180 degrees from the zero degree radial marker-extension; and a 90 degree radial marker-extension of the plurality of radial marker-extensions that is configured to extend substantially 90 degrees from the zero degree radial marker-extension and further comprising a 270 degree radial marker-extension of the plurality of radial marker-extensions that is configured to extend substantially 270 degrees from the zero degree radial marker-extension.

2. The multi-axis tumor marker system of claim 1, further comprising a guide head configured to guide the marker-extensions radially outward, said guide head comprising a radial guide along a radial guide aperture.

3. The multi-axis tumor marker system of claim 1, wherein the marker is a phase change marker and wherein the phase change marker is a liquid in the marker extension and wherein the phase change marker changes to a solid upon deposition in said margin tissue.

4. The multi-axis tumor marker system of claim 1, wherein the phase change marker comprises a radiopaque material.

5. The multi-axis tumor marker system of claim 1, wherein the phase change marker comprises an adhesive.

6. The multi-axis tumor marker system of claim 5, wherein the phase change marker comprises a radiopaque material.

7. The multi-axis tumor marker system of claim 5, wherein the phase change marker comprises a cyanoacrylate adhesive.

8. The multi-axis tumor marker system of claim 7, wherein the phase change marker comprises a radiopaque material.

9. The multi-axis tumor marker system of claim 1, wherein the marker-extension comprises shape memory metal that is configured to extend radially outward from the distal end opening of the catheter.

* * * * *